(12) United States Patent
Brendel et al.

(10) Patent No.: US 10,740,932 B2
(45) Date of Patent: Aug. 11, 2020

(54) METHOD FOR THE RECONSTRUCTION OF QUANTITATIVE IODINE MAPS USING ENERGY RESOLVED TOMOGRAPHY

(71) Applicant: KONINKLIJKE PHILIPS N.V., Eindhoven (NL)

(72) Inventors: Bernard Johannes Brendel, Norderstedt (DE); Michael Grass, Buchholz in der Nordheide (DE); Peter George Van De Haar, Eindhoven (NL); William Edward Peter Van Der Sterren, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/551,202

(22) PCT Filed: Feb. 18, 2016

(86) PCT No.: PCT/EP2016/053485
§ 371 (c)(1),
(2) Date: Aug. 15, 2017

(87) PCT Pub. No.: WO2016/135044
PCT Pub. Date: Sep. 1, 2016

(65) Prior Publication Data
US 2018/0040146 A1   Feb. 8, 2018

(30) Foreign Application Priority Data

Feb. 25, 2015 (EP) .................................... 15156455

(51) Int. Cl.
*G06T 11/00* (2006.01)
*G06T 7/00* (2017.01)
(Continued)

(52) U.S. Cl.
CPC .............. *G06T 11/006* (2013.01); *A61B 6/03* (2013.01); *A61B 6/467* (2013.01); *A61B 6/481* (2013.01);
(Continued)

(58) Field of Classification Search
None
See application file for complete search history.

(56) References Cited

U.S. PATENT DOCUMENTS

| 8,923,583 | B2 | 12/2014 | Thibault | |
| 2004/0101088 | A1* | 5/2004 | Sabol | A61B 6/481 378/4 |
| 2013/0343624 | A1* | 12/2013 | Thibault | G06T 11/006 382/131 |

FOREIGN PATENT DOCUMENTS

| WO | 2010001281 A1 | 1/2010 |
| WO | 2014170780 A1 | 10/2014 |

OTHER PUBLICATIONS

Long, Yong et al "Multi-Material Decomposition using Statistical Image Reconstruction for Spectral CT", IEEE Transactions on Medical Imaging, vol. 33, No. 8, Aug. 2014, pp. 1614-1626.
(Continued)

*Primary Examiner* — Matthew C Bella
*Assistant Examiner* — Brian D Shin (57) ABSTRACT

An image processing system (IPS) and related method for image reconstruction operations, in particular for spectral computed tomography imaging. The image reconstruction operation is based on optimizing a regularized objective or cost function. The objective function includes a regularization term (R) that incorporates, as a-priori knowledge, a known amount of a material resident within a field of view to be reconstructed.

16 Claims, 3 Drawing Sheets

(51) Int. Cl.
*A61M 31/00* (2006.01)
*A61B 6/00* (2006.01)
*A61B 6/03* (2006.01)
*A61F 2/82* (2013.01)

(52) U.S. Cl.
CPC ............... *A61B 6/482* (2013.01); *A61F 2/82* (2013.01); *A61M 31/005* (2013.01); *G06T 7/0012* (2013.01); *A61F 2250/0098* (2013.01); *G06T 2207/10081* (2013.01); *G06T 2207/30052* (2013.01); *G06T 2210/41* (2013.01); *G06T 2211/408* (2013.01); *G06T 2211/424* (2013.01)

(56) References Cited

OTHER PUBLICATIONS

Schirra, Carsten, O. et al "Statistical Reconstruction of Material Decomposed Data in Spectral CT", IEEE Transactions on Medical Imaging, vol. 32, No. 7, Jul. 2013, pp. 1249-1257.

\* cited by examiner

METHOD FOR THE RECONSTRUCTION OF
QUANTITATIVE IODINE MAPS USING
ENERGY RESOLVED TOMOGRAPHY

CROSS-REFERENCE TO PRIOR
APPLICATIONS

This application is the U.S. National Phase application under 35 U.S.C. § 371 of International Application No. PCT/EP2016/053485, filed on Feb. 18, 2016, which claims the benefit of European Patent Application No. 15156455.6, filed on Feb. 25, 2015. These applications are hereby incorporated by reference herein.

FIELD OF THE INVENTION

The invention relates to an image processing system, to an image processing method, to a computer program product, and to a computer readable medium.

BACKGROUND OF THE INVENTION

In spectral (or multi-energy) imaging one can reconstruct for physical object properties of interest such as photo effect, Compton scattering, water content, bone content, iodine content, etc. But due to the fact that for many spectral tomographic X-ray setups the overlap of the X-ray spectra used for acquisition is quite large, the reconstruction problem is ill posed and this may lead to the occurrence of, on occasion severe, noise in the resulting images. In order to combat noise build-up, iterative reconstruction for spectral X-ray tomography is of increasing interest. In iterative reconstruction noise can be reduced by giving more weight to data with good signal-to-noise ratio, but also by applying regularization functions. These regularization functions allow incorporating a priori information about the object into the reconstruction. In most cases they enforce smoothness (to reduce noise) or similarity to a given image.

As mentioned above, with spectral X-ray tomography it is possible to reconstruct physical properties of the object. Of great interest in this context is for instance the spatial distribution of a certain material of interest to so construct so called material maps. A non-limiting example is for instance "contrast agent maps" such as "iodine maps". Such contrast agents are administered before or during imaging to increase image contrast for soft tissue for instance. However, even with iterative reconstruction, there are still cases where such reconstructed material maps are of comparably poor quality.

SUMMARY OF THE INVENTION

There may therefore be a need in the art for an alternative image processing method or related system.

The object of the present invention is solved by the subject matter of the independent claims where further embodiments are incorporated in the dependent claims.

It should be noted that the following described aspect of the invention equally applies to the image processing method, to the computer program product, and to the computer readable medium.

According to a first aspect of the invention, there is provided an image processing system, comprising:

an input port for receiving at least one input image acquired by an imager of a specimen that includes at least a first material;

an image reconstructor configured to reconstruct the at least one input image into at least one reconstructed image representative of a distribution of said first material or of a second material of the specimen;

wherein operation of the reconstructor is driven by a regularized objective function that includes a regularizer function;

wherein the regularizer function includes at least one material term with a parameter representative of an amount of at least said first material in at least a part of the specimen.

In other words, the regularizer function as proposed herein operates to regulate or "control" or at least influence the reconstructed amount of the material as per the reconstructed image(s) to so "enforce" conformity with the known or predefined material amount present in the field of view of the used imaging modality at the time of image acquisition.

In one embodiment, there are a plurality of different material types (that is a first, second, third, etc.) of interest present in the specimen. The proposed system is adaptable to this as the regularizer function may include in this multi-material case a plurality of different material terms, one or more for some or each material type.

Although in general, all materials of interest are regularized (that is, their amounts are included as constraints in their respective material term of the regularizer function), this may not necessarily be so in all embodiments. For instance, in some embodiments, only a subset of the materials of interest are regularized. Also, in some embodiments, one may wish to regularize for one material, say the first material, but the actual material of interest is the second material and it is the second material that is reconstructed and/or output by the system. However, in general it may be beneficial to reconstruct for all those materials that are regularized.

According to one embodiment the material term represents a deviation of an estimated amount for said first material from said material parameter.

According to one embodiment the at least one input image of the specimen is acquired at a field of view, wherein the material term of the regularizer function is restricted to image elements that represent only a part of said specimen. This restriction can be achieved for instance by masking certain voxel regions which represent materials or tissue types that are known to induce a crosstalk signal into the material image to be reconstructed and thus may distort any image based measurement of the reconstructed amount of contrast agent.

According to one embodiment the reconstructor is configured to implement an iterative reconstruction algorithm, wherein the estimated amount for said one or more materials is computed by the reconstructor in one or more iterations.

According to one embodiment the imager is a spectral imager having an energy resolving detector, wherein the at least one input image is obtained from image signals detected at said energy resolving detector.

According to one embodiment the imager includes an X-ray source operable at different voltages wherein the at least one input image is obtained from image signals detected at a detector of said imager for said different voltages.

According to one embodiment the at least one input image is a projection image of the specimen.

According to one embodiment the imager is a computed tomography scanner or a C-arm X-ray system.

According to one embodiment the first material is confined to a portion of said specimen within a field of view of said imager.

According to one embodiment the first material is an imaging contrast agent.

According to one embodiment the contrast agent is included in one or more drug-eluting non-native bodies resident in the specimen.

According to one embodiment the contrast agent is included in a stent structure resident in the specimen.

According to one embodiment the image processing system comprises a user interface configured to allow a user to specify the at least one parameter.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
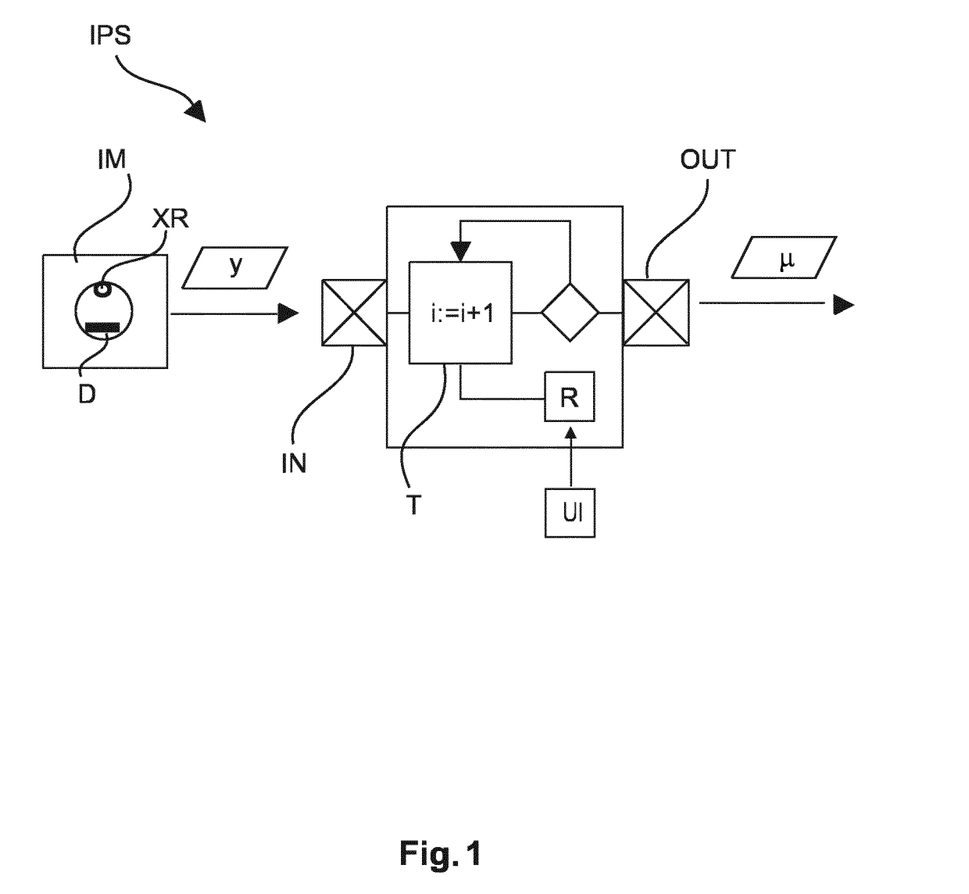
FIG. 1 shows a schematic diagram of an imaging arrangement.

FIG. 1 shows a schematic block diagram of an imaging arrangement. The arrangement includes an imaging modality IM and an image processing system component IPS.

The imaging modality IM supplies input images acquired of a specimen (such as a human or animal patient or an inanimate object such as an item of luggage) and said input images can be processed by the image processing system component IPS to be described in more detail below. Types of imaging modalities IM envisaged herein include X-ray imaging modalities such as a CT scanner or an interventional C-arm imager. X-ray based imaging modalities include an X-ray source XR and a detector D. During image acquisition, the specimen (not shown) resides in an examination region of the imaging modality between the X-ray source and the detector D. X-ray radiation is emitted from the source XR, interacts (e.g., is attenuated) with the specimen and is then detected at detector D as electrical signals. Conversion circuitry then converts said electrical signals into the input images. Other, non-X-ray imaging modalities are likewise envisaged herein, for instance PET (positron-emission-tomography) and/or MR (magnetic resonance) imagers.

The input images of the specimen are acquired at one or more field-of-views (FOV) to image at least a certain region of interest (ROI). Acquisition of such input images may be occasioned in medical contexts, such as during a medical intervention. Exemplary interventions are TACE (transcatheter arterial chemoembolization) or PCI (percutaneous coronary intervention). At least the ROI is usually made up from different material types such as water, fat etc. Frequently, there are also one or more foreign materials present in the ROI during the image acquisition such as one or more previously administered imaging contrast agents (such as Iodine and/or Gadolinium or others) to enhance image contrast.

To be able to better image the respective distributions of these materials of interest (in particular, but not only, of the one or more contrast agent(s)) within the ROI, the imaging modality IM is configured for spectral imaging in one embodiment. Examples are spectral CT/C-arm or CT/C-arm dual/multi-energy imaging.

In spectral (or multi-energy) C-arm or CT, multiple projection images are acquired, which represent the attenuation properties of the scanned object for different X-ray spectra. The spectral imaging can be achieved in different ways all of which are envisaged herein. For instance, the detector D of the CT or C-arm modality (or "imager") may be of a photon-counting type which allows acquiring the projection images per energy value in a single exposure for a given projection direction. In the context of photon-counting detectors, these energy values are frequently referred to as "bins". Alternatively, the imager IM includes an X-ray source that is operable at different voltages and the material projection images are then acquired in multiple exposures (one or more at each of the different voltages) per projection direction by switching the X-ray tube accordingly. In the CT or C-arm imaging with X-ray tube voltage switching, multiple energy images are acquired from different projection directions. In CT or C-arm imaging with photon-counting detectors, there is a plurality of input images: one or more images for different projection directions, and, for each projection direction there are two or more energy images for different energy values or intervals.

No matter the spectral imaging technique used, based on these multiple projection input images, physical object properties can be reconstructed for. E.g. one may wish to reconstruct cross-sectional images for photoelectric effect scattering or Compton scattering contributions or for different materials, such as water content, bone content, iodine content. The number of bins or different tube voltages corresponds to the maximum number of basis material or physical properties for which one wishes to reconstruct for. Two bins or two different voltages (hence sometimes referred to as "dual" energy imaging) are usually used but any number of bins/voltages such as 3, 4 or 5 or indeed any whole number of energy bins/voltages are envisaged herein.

The image reconstruction is carried out by the image processing system IPS. To this end, the image processing system IPS includes an image reconstruction component RECON whose operation is based in one embodiment on a numerical optimization scheme driven by a suitable objective function L.

The objective function is regularized, that is, it includes as a functional component a regularization or penalty function R. The regularization function (also referred to as "regularizer") is used to enforce one or more desirable properties of the solutions (that is, of the reconstructed one or more images) to be obtained. The structure of the regularizer R and the properties enforced will be explained in more detail below.

In operation, the image processing system IPS receives at its input port IN the one or more input images represented herein collectively as "measurement data" y. The transformer T then operates using a suitable solution algorithm to, in one embodiment, iteratively search for solutions (that is, images representing spatial distributions of physical properties of the object) in a 3D "image domain". This search algorithm is configured to return solutions that improve the objective function L. In other words, L "drives" the optimization. In one embodiment, the search operation may include iterating through one or more intermediate images $\mu_i$ where the subscript i denotes the iteration number, but one step, non-iterative, regularized solution algorithms are also envisaged herein. At the conclusion of the reconstruction operation (e.g. at the conclusion of one or more iterations), one or more reconstructed images $\mu_m$, per material m (e.g., a water distribution image $\mu_w$ and a contrast agent distribution image $\mu_I$, respectively) are output at output port OUT.

The respective one or more material images (sometimes referred to as "material maps", e.g. iodine maps) $\mu_m$ obtained from the reconstruction operation provides to the user (e.g., the interventional radiologist) clues about the spatial distributions of the respective material in the ROI. The output 3D volume reconstructions (or cross sectional view thereacross) may then be displayed separately for a desired one of the material m or may be displayed together on a display unit during the intervention to check proper deployment of a stent for instance. Alternatively, the 3D volume reconstructions may be displayed after the intervention for review or teachings purposes.

Applicants found a new class of regularization functions R that have been observed to yield high fidelity output imagery. It is proposed herein to model prior knowledge into the objective function on which the reconstructor RECON is based. In particular, the prior knowledge is modelled into the structure of the penalizer or regularizer R. More particularly, it is proposed herein to incorporate into the reconstruction operation an a-priori-known amount of one or more of the materials of interest within the volume to be reconstructed. The newly proposed regularization function is configured to penalize a difference between the reconstructed amount of a certain material of interest (e.g. a contrast agent) and the known amount of said material that is known to be present within the FOV of the imager during acquisition of the input images.

Figure 2:
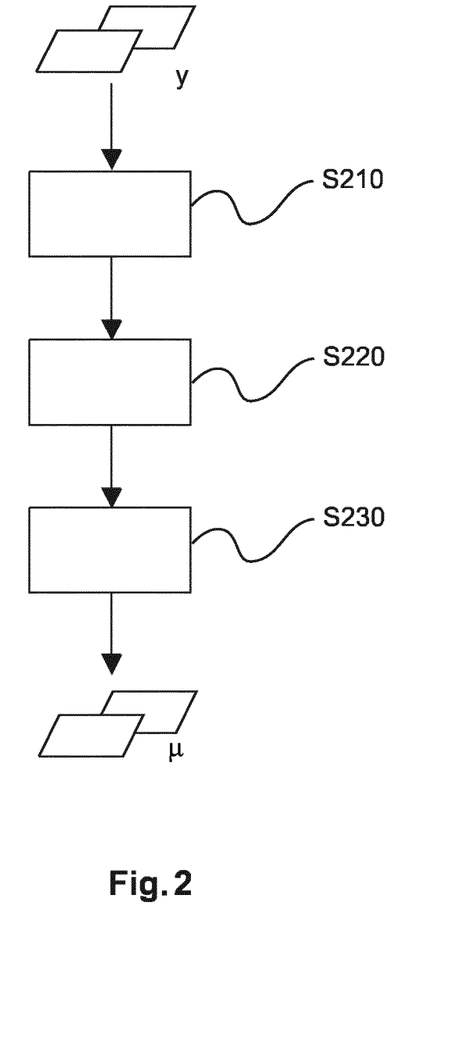
FIG. 2 shows a flow chart of an image processing method.

Operation of the proposed image processing system IPS will now be explained in more detail below at flow chart of FIG. 2.

Energy resolved input images (such as projection images) y are received at step S210. The input images have been acquired by suitable spectral imaging modalities as introduced above at FIG. 1.

At step S220 the input images for the different energies (and hence material of interest) are then reconstructed using an iterative reconstruction algorithm. The reconstruction algorithm is based on optimizing a regularized cost or objective function L.

The so reconstructed material images or maps are then output at step S230.

The term "reconstruction" as used herein refers to a transformation from projection domain (the 2D space formed by the detector pixels) to a 3D image domain. This is essentially an imaginary 3D grid in space between the X-ray source and the detector of the imaging system. Reconstruction essentially amounts to the population of points (voxels) of this grid with values that explain the projection images.

The iterative transformation includes an update function that is derived by applying a suitable solution algorithm (such as Newton-Raphson, conjugate gradients, and others) to the objective function F (which in this context is usually referred to as a cost function) with the regularization term R.

A typical regularized cost function L for the iterative reconstruction in spectral X-ray tomography is given exemplarily (and in no way limiting) for a reconstruction of a water image and an iodine image as:

$$L = -\log(P(\mu_w, \mu_I | y)) + R(\mu_w, \mu_I) \quad (1)$$

In (1), L is the so called penalized log-likelihood function. P(.) is a probability measure of the images $\mu_w$ and $\mu_I$, given the measured X-ray intensities y, that is, the input images. The probability measure is in general dependent on specifics of the detector and of the physical effect one wishes to image for. P may also include a noise model, for instance, for transmission imaging with a photon-counting detector, P may be taken to have a Poisson density.

The function R(.) represents the regularization function, which itself may comprise several regularization terms.

Iterative reconstruction is performed by optimizing the cost function with respect to the 3D material images $\mu_w$, and $\mu_I$.

$\mu_I$ is a vector including the iodine concentration $\mu_{Ij}$ in each voxel j in image space, and similar for the water image $\mu_w$.

In an iterative setting, there is a corresponding iterative update function that may be written as $$\begin{pmatrix} \mu_I^{i+1} \\ \mu_w^{i+1} \end{pmatrix} = f_{update}(\mu_I^i, \mu_w^i)$$

for some functional expression $f_{update}$ which relates to the particulars of the solution algorithm used. Again, index i denotes an iteration step. The iterative processing of the input imagery y via one or more intermediate images $\mu_I^i, \mu_w^i$ by operation of update function $f_{update}$ amounts to a simultaneous optimization of L for each material of interest. If the objective function L is separable, the optimization may alternatively be executed as two or more separate optimization problems (one for each material channel m).

Turning now in more detail to the structure of a regularizer term included in regularizer R, the total amount of reconstructed material, say contrast agent I (iodine say as a non-limiting example), can be calculated as follows:

$$a_I = \sum_{j \in F_C} \mu_{Ij} \cdot V_j \quad (2)$$

$a_I$ being the total amount of reconstructed contrast agent and $V_j$ being the volume of voxel j. $F_C$ is the set of voxels that is known to potentially contain contrast agent. In words, the amount is the sum over products of volume elements and (local) concentrations. Preferably, the sum is taken only over locations that are known to potentially contain contrast agent but a summation over the whole volume are not excluded herein.

According to one embodiment, voxel regions which are known to potentially contain crosstalk signals can be masked to be excluded from the summation in (2). For instance, in one example voxels that represent bone attenuation contributions are masked, because they are known to produce crosstalk in iodine maps for an iodine-water separation. It will be understood that "bone masking" is merely an illustration in that in other contexts other voxel signals may be masked. However the masking operation is optional and in other embodiments the summation in (3) extends over all voxels within the reconstructable volume (that is those voxels whose projection falls within the FOV) so there is no masking out of voxels. The set of voxels to be masked (that is, the set-theoretic complement of $F_C$) can be established for instance by using a grey-value thresholded segmentation that is run on a conventional filtered-backprojection (FBP) volume reconstruction obtained from the measured projections y.

If the known amount (as measured for instance in Mol or in a suitable mass unit such as milligram or gram etc.) of iodine is specified by material parameter $b_1$, a possible regularization term for material α (=iodine in this exemplary case) may be implemented as:

$$R_\alpha = \beta \left| \sum_{j \in F_C} \mu_{Ij} \cdot V_j - b_I \right|^p \quad (3)$$

wherein p is an adjustable exponent, which if preferably set within the interval [1, 2] to ensure convexity of the cost-function. $\beta$ is an adjustable parameter (unity not being excluded herein) to control the influence of this regularization term. It will be understood that the regularizer terms $R_\alpha$ may be added to the other terms in the regularization function R( ) to thereby incorporate the knowledge about the known amounts of materials of interest into the iterative reconstruction process. For a given material $\alpha$, an algorithmic implementation of the regularizer term includes forming the difference between a known amount of material (eg contrast) agent, and estimated amount for the know amount of material. The estimated amount can be constructed as before in (2), by summing over products of concentrations and volume elements. The summation may extend across the whole or a part of the volume to be reconstructed. Specifically, for computational efficiency, the sum may be run only over those locations $F_C$, which can be expected to actually include the contrast agent.

The material regularization term as per eq (3) can be seen to effectively quantify a deviation of the estimated amount $\mu_{mi}$ of the material of interest m (as computed during the one or more iterations i) from the known amount of the respective material. Put differently, the material regularization term (3) induces or facilitates a converging behavior of the optimization problem as per eq (1) towards solutions that represent the respective material at the pre-defined amount b. In this sense, the material term (3) controls or regulates the amount of reconstructed material in the reconstructable output image. For instance, out of two solution images that would otherwise return the same unregularized cost (that is, if one were to ignore the regularizer R contribution), the iterative optimization will converge to the one that is numerically closer to the known contrast agent deposition precisely because of the effect of the regularizer R proposed herein.

The material amount parameters $b_m$ (e.g. $b_1$ for iodine as in the example above) are either a-priori known by the user and are manually supplied by the user to the IPS. In one embodiment, the system provides a user interface UI through which the user can supply the one or more respective material amount parameters $b_m$ for the respective materials of interest. For instance, the user interface UI may be provided as a graphical user interface with suitable widgets such as sliders, textboxes, drop-down menus, etc. where the user can specify the respective amounts (in a suitable unit as mentioned before). The so specified parameter(s) are/(is) then forwarded to reconstructor RECON to accordingly populate the regularizer terms(s) of the objective function L. In other embodiments, the material amount parameters $b_m$ may be procured by the IPS interfacing with the electronics of an injection apparatus used for the administration of the contrast agent.

As briefly indicted above the regularizer R may in general include more than one material terms (3) for different materials of interest $\alpha$. Also, the materials of iodine and/or water are merely exemplary and other material of interest may be used in addition or instead to water and/or Iodine. In particular in some embodiments, there are more than one contrast agent (for instance iodine and gadolinium) each having their respective regularizer term similar to eq (3) above. However it may not be necessary to have a material amount regularizer (3) term incorporated in the regularizer R for all materials of interest. For instance, it may be beneficial to have only, say, the contrast agent amount regularized by a term (3), although one is interested in a material other than the contrast agent. For instance, one may wish to reconstruct for the water content/distribution although it is only the iodine that is regulated as per (3). The regularization in respect of only one material (from a plurality of materials) may be sufficient in some circumstance as the higher fidelity in the reconstruction caused by the regularization of the other material amount still feeds through to the reconstructions of the other materials. In other words, the iterative reconstruction algorithm may converge towards a good solution for all materials of interest although one regularizes merely for some (for instance a single one) but not all materials of interest.

Also, it will be understood that the regularizer R may include other regularizer terms in addition to the material amount terms (3). For instance, other terms may be configured to enforce certain desired smoothness properties quantified by a suitable metric that capture other forms of a-priori knowledge, e.g. in relation to image features (such as edges), etc.

Also, it will be understood that the formulation of the regularizer in terms of a log-likelihood expression is but one embodiment and non-statistical approaches are likewise envisaged herein.

In the above mentioned X-ray based system, the input images are the projection images for the various energy bins and the material decomposition model and the computation of the material distribution images is achieved during the reconstruction. As a variant to this, the measured projection images may be converted first by a material decomposition algorithm to obtain one or more material projection images before using it/them as input images for the reconstruction described above.

Although the proposed method has been explained for X-ray based transmission imaging modalities (in particular CT), the principles as described herein can be readily applied to emission reconstruction algorithms as in PET or MR imaging. In PET/MR reconstructions, the input images y are projections of the distribution of ta radioactive tracer inside the patient and the Fourier-transform of the proton density of the patient (or other quantities related to the protons). The reconstructed images are the spatial distribution of the radioactive tracer and the protons inside the patient.

The proposed method and system has been found to be of particular benefit when the material of interest is confined to a known volume portion in the imager's image domain during the image acquisition. For instance, rather than injecting the contrast agent in liquid form into the patient's vasculature, there are applications where the contrast agent bound to solid carriers that lodge into place at the ROI. For instance, in TACE procedures, so-called imageable bead may be used. These beads are in one embodiment formed as relatively small sphere structures which are applied to a tumor via a catheter to embolize the tumor. The beads include (for example are coated with) a contrast agent material such as iodine to render the beads visible under X-ray and the beads includes in addition a chemotherapeutic agent to treat the tumor. Alternatively, the contrast agent is embedded within the bead material (or the beads are formed entirely from a contrast agent material) and it is the outer surface of the beads that are coated with the chemotherapeutic agent. Since, due to their size, the spheres cannot escape with the blood-flow through the capillaries the total amount of contrast agent is concentrated inside the tumor and therefore, inside the field of view when performing a 3D cone beam C-arm CT scan. Voxels that represent bone regions can be excluded e.g. by using a model based bone removal algorithm. Also, in this case the definition of the masked voxels can be achieved by a segmentation of the tumor tissue which can be done manually or automatically on a scout reconstruction volume.

Figure 3:
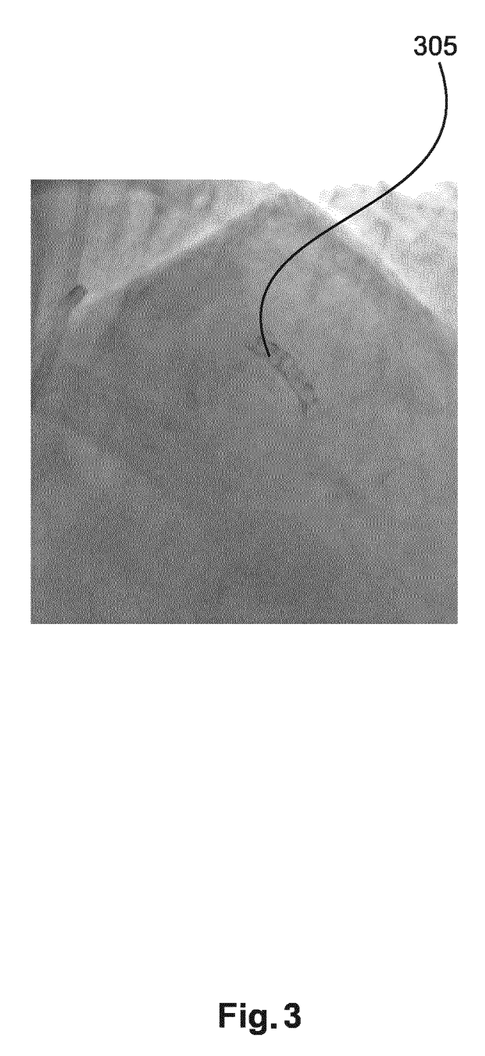
FIG. 3 shows an X-ray projection image of a medical device doped with contrast agent.

An alternative application is PCI where a 3D C-arm CT or spectral CT imaging of the patient is carried out whilst a bioabsorbable iodine doped scaffold or stent resides inside a patient artery. An X-ray projection in FIG. 3 illustrates this situation where a footprint 305 of a scaffold or stent structure is shown. The stent includes (e.g., on its outer surface and or within) a well-defined and known amount of iodine and this property can well be used as for material amount regularization as described above in the 3D reconstruction from energy resolved CT or C-arm CT image data. Preferably but not necessarily in all embodiments, the stent is formed from a bioabsorbable material. For both applications, TACE with imageable beads and PCI with bioabsorbable stents, the same regularization principle can be applied for iterative projection decomposition of dual energy projections. As described above, the projection input images y can be acquired with a C-arm system or CT system using either tube voltage (kV) switching or energy resolving detectors.

It should be appreciated that the terms "optimization" or "optimizer" as used above designate a numerical optimization scheme. This does not necessarily imply that the output images are optimal in an absolute sense. For one reason, the solution algorithm used may not necessarily converge during iteration towards a global minimum but may converge to a local minimum. Second, even if the iterations were to converge to the global minimum, the iterations herein may be aborted after a few iterations, to save resources or for whatever reason. For instance, one abort condition may be that iterations are to halt if there is no significant change at the output after a pre-defined number of iteration steps. In yet other words, the reconstructed material images $\mu_m$, produced at the output of the proposed image processing system or by way of the described method are not necessarily the best possible solutions but may be acceptable approximations thereof in the relevant context or circumstance.

It will also be appreciated that, because of the material amount regularization, the reconstruction results will in general depend on the specified material amount parameters bm. In other words, a variation of one or more of the material amount parameters bm will cause a variation in one or more of the reconstructed material images.

The image processing system IPS may be arranged as a software module or routine with suitable interfaces (such as input port IN and output port OUT) and may be run on a general purpose computing unit or a dedicated computing unit. For instance image processing system IPS may be executed on a workstation or operator console associated with the or another imaging modality IM. The image processing system IPS with some or all of its components may be resident on the executive agency (such as a general purpose computer, workstation or console) or may be accessed remotely/centrally by the executive agency via a suitable communication network in a distributed architecture. The components may be implemented in any suitable programming language such as C++ or others.

In one embodiment, the components of the image processing system IPS may be arranged as dedicated FPGAs (field-programmable gate array) or similar standalone computing chip or device. In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an"

does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
    a first input port for receiving at least two projection images, wherein the at least two projection images are based on different energy values of X-ray radiation interacting with a specimen that includes a first material, the at least two projection images having been acquired by an imager;
    a second input port for receiving a material parameter indicating a measured amount of at least said first material, wherein the measured amount of at least said first material is measured independent of the at least two projection images; and
    an image reconstructor configured to reconstruct the at least two projection images into at least one reconstructed image representative of a distribution of said first material or of a second material of the specimen;
    wherein operation of the reconstructor is driven by a regularized objective function that includes a regularizer function;
    wherein the regularizer function includes at least one material term with said material parameter indicating the measured amount of at least said first material in at least a part of the specimen.

2. Image processing system as claimed in claim 1, wherein the at least one material term represents a deviation of an estimated amount for said first material from said material parameter.

3. Image processing system as claimed in claim 2, wherein the reconstructor is configured to implement an iterative reconstruction algorithm, wherein the estimated amount for said first or second material is computed by the reconstructor in one or more iterations.

4. Image processing system as claimed in claim 3, wherein the at least two projection images of the specimen are acquired at a field of view, wherein the at least one material term of the regularizer function is restricted to image elements that represent only a part of said specimen.

5. Image processing system as claimed in claim 4, wherein the imager (IM) is a spectral imager having an energy resolving detector, wherein the at least two projection images are obtained from image signals detected at said energy resolving detector.

6. Image processing system as claimed in claim 5, wherein the imager includes an X-ray source operable at different voltages wherein the at least two projection images are obtained from image signals detected at a detector of said imager for said different voltages.

7. Image processing system as claimed in claim 1, wherein the at least two projection images are projection images of the specimen.

8. Image processing system as claimed in claim 1, wherein the imager is a computed tomography scanner or a C-arm X-ray system.

9. Image processing system as claimed in claim 8, wherein the first material is confined to a portion of said specimen within a field of view of said imager.

10. Image processing system as claimed in claim 9, wherein the first or the second material is an imaging contrast agent.

11. Image processing system as claimed in claim 10, wherein the contrast agent is included in one or more drug-eluting non-native bodies resident in the specimen.

12. Image processing system as claimed in claim 1, wherein the contrast agent is included in a stent structure resident in the specimen.

13. Image processing system as claimed in claim 1, comprising a user interface configured to allow a user to specify said material parameter.

14. An image processing method comprising acts of:
    receiving at least two projection images, wherein the at least two projection images are based on different energy values of X-ray radiation interacting with a specimen that includes a first material, the at least two projection images having been acquired by an imager;
    receiving a parameter indicating a measured amount of at least said first material, wherein the measured amount of at least said first material is measured independent of the at least two projection images; and
    performing a reconstruction operation to reconstruct the at least two projection images into at least one reconstructed image representative of a distribution of said first material or of a second material of the specimen;
    wherein the reconstruction operation is driven by a regularized objective function that includes a regularizer function;
    wherein the regularizer function includes at least one material term with said parameter indicating the measured amount of at least said first material in at least a part of the specimen.

15. A computer program element for controlling a system, which, when being executed by a processing unit, is adapted to perform the method acts of claim 14.

16. A non-transitory computer readable medium having stored thereon the program element of claim 15.

* * * * *